United States Patent [19]

Blum

[11] 4,314,971

[45] Feb. 9, 1982

[54] MOLECULAR SEPARATION AND ISOENZYME ANALYZERS

[76] Inventor: Alvin S. Blum, 2350 Del Mar Pl., Ft. Lauderdale, Fla. 33301

[21] Appl. No.: 209,838

[22] Filed: Nov. 24, 1980

Related U.S. Application Data

[63] Continuation-in-part of Ser. No. 898,998, Apr. 21, 1978, Pat. No. 4,264,327, Ser. No. 968,907, Dec. 13, 1978, Pat. No. 4,254,084, and Ser. No. 972,670, Dec. 26, 1978, Pat. No. 4,259,079.

[51] Int. Cl.³ .................. G01N 33/56; G01N 35/08
[52] U.S. Cl. .................. 422/82; 204/108 G; 422/81; 435/808; 435/291
[58] Field of Search .......... 23/230 R, 230 B; 422/81, 82; 204/180 G; 435/291, 808

[56] References Cited

U.S. PATENT DOCUMENTS 3,320,148  5/1967  Skeggs .................. 422/82 X

Primary Examiner—Ronald Serwin

[57] ABSTRACT

Automatic analyzer including controlled dispensing and mixing of sample and reagents. Novel electroseparation process for separating certain molecules from other molecules in flowing streams. Apparatus for adding substrate, mixing and temperature control of separated isoenzyme streams. Apparatus for directly measuring change of optical properties of the streams with direct readout of results.

15 Claims, 9 Drawing Figures

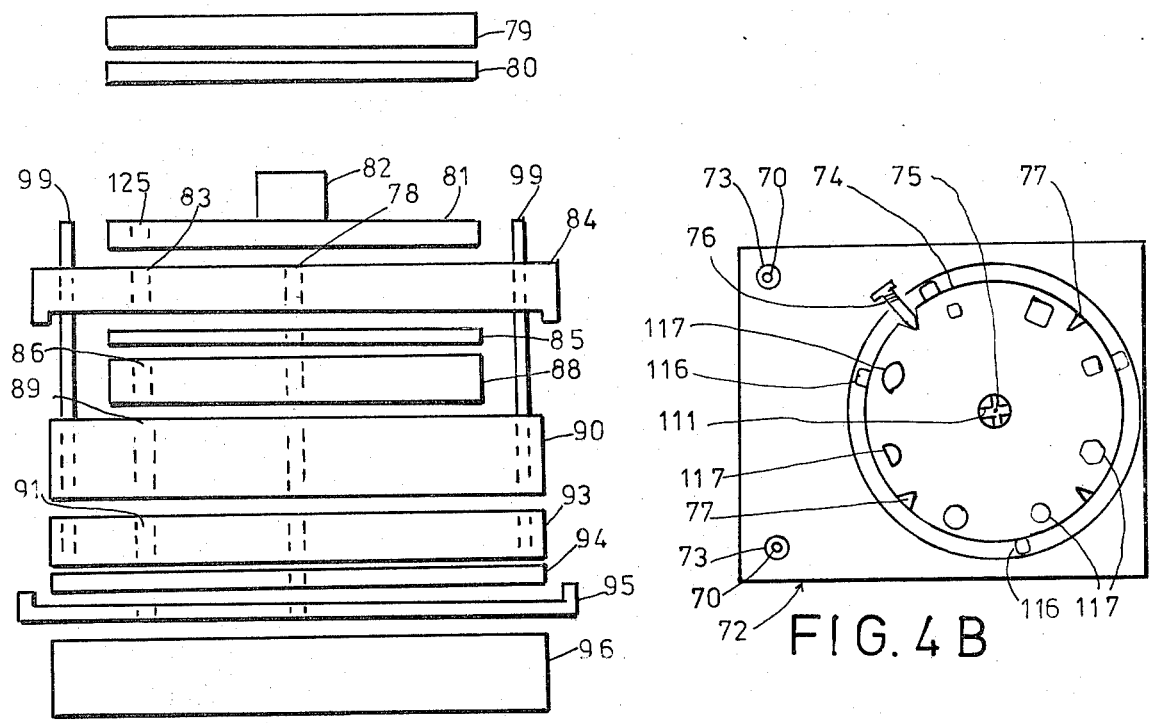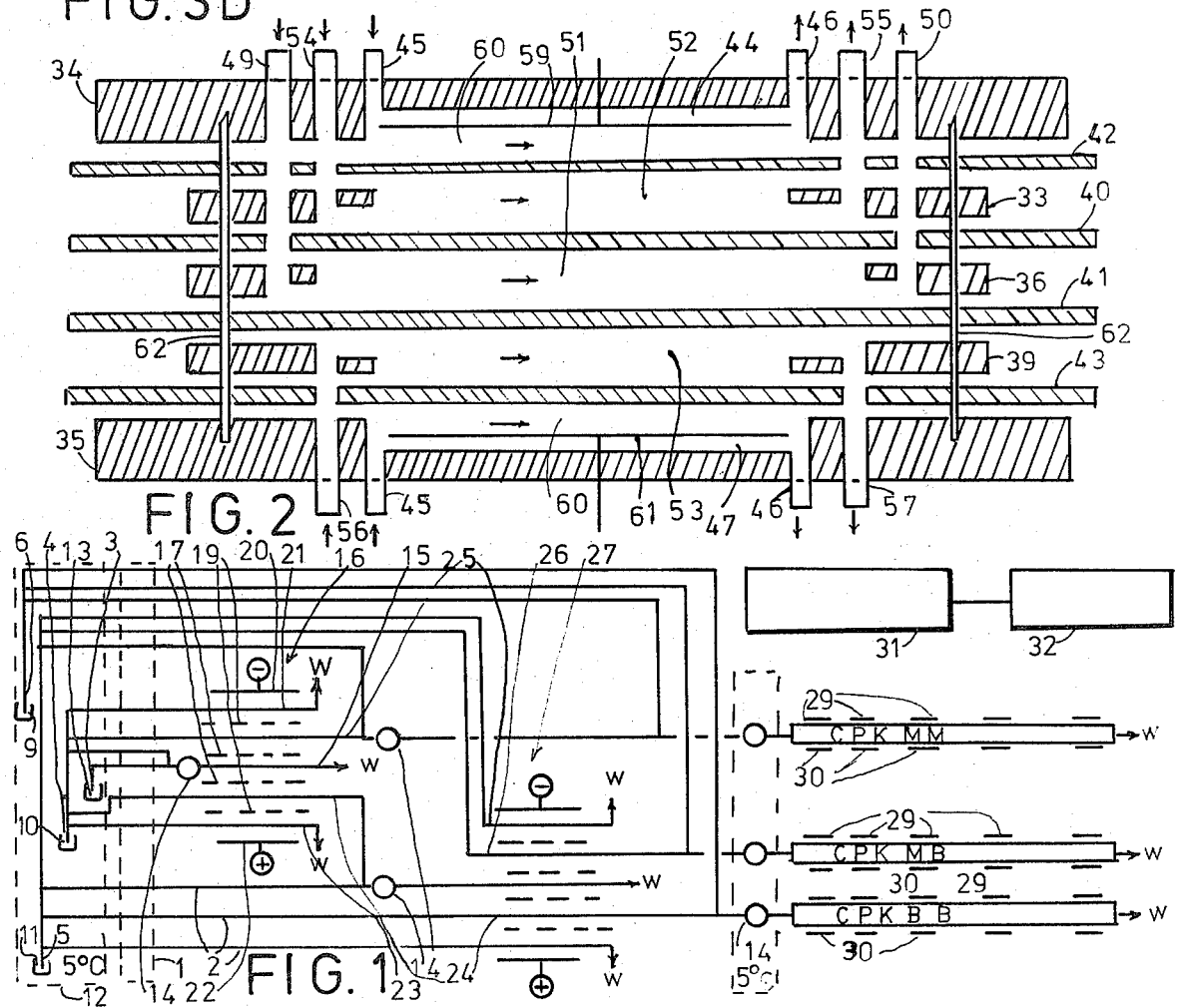

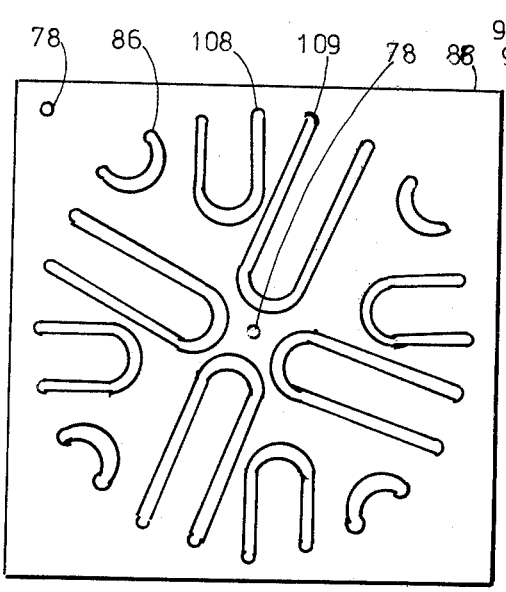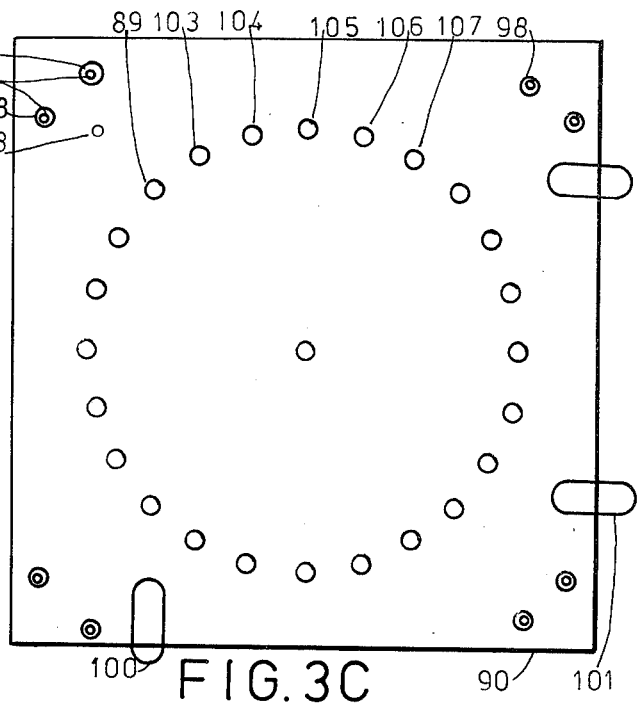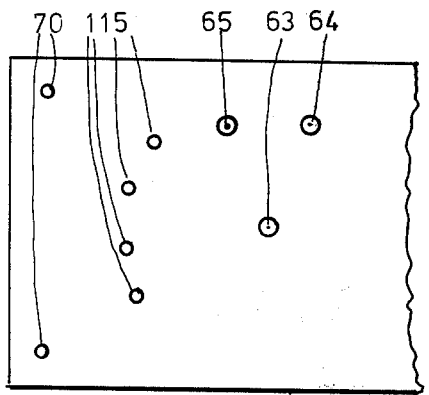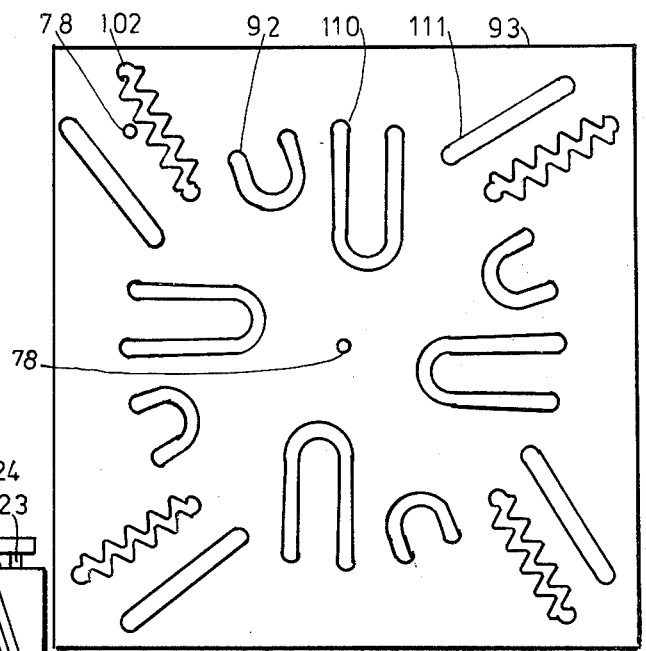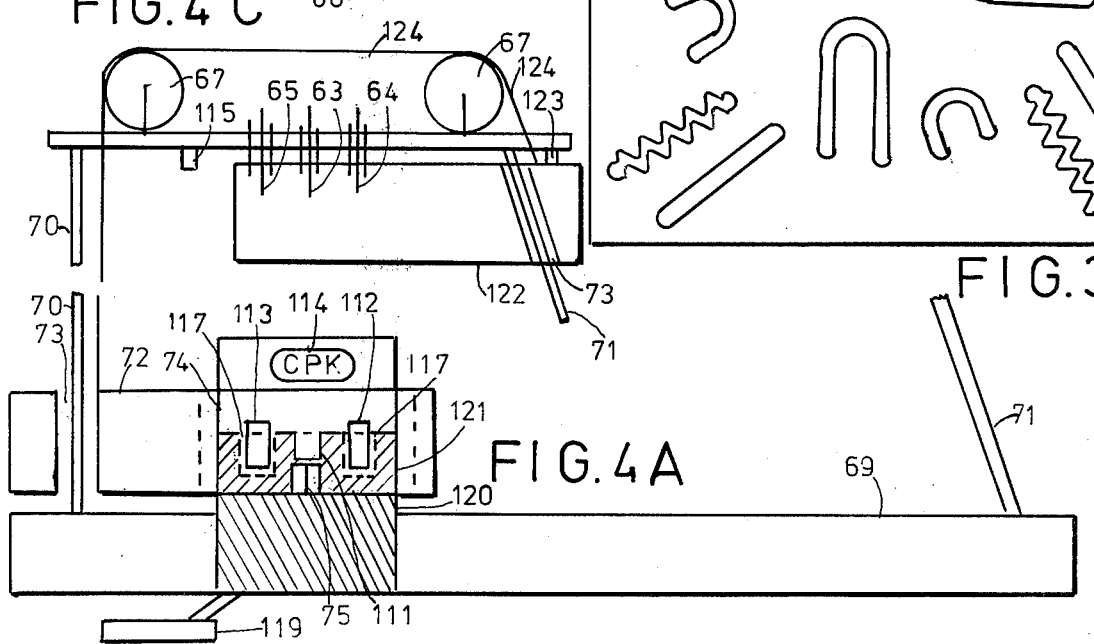

MOLECULAR SEPARATION AND ISOENZYME ANALYZERS

This is a continuation in part of copending applications Ser. Nos. 898,998 filed Apr. 21, 1978, 968,907 filed Dec. 13, 1978 and 972,670 filed Dec. 26, 1978. These are now U.S. Pat. Nos. 4,264,327, 4,254,084 and 4,259,079 respectively.

This invention relates to flowing fluid automatic analyzers employing electrical separation for measuring the concentration of certain molecules in a mixture of molecules or for measuring the relative concentrations of several different molecules such as isoenzymes or serum proteins.

DESCRIPTION OF THE PRIOR ART

Certain clinical analyses require separation of molecules from other constituents of a sample or the separation of certain types of molecules from one another prior to their detection and quantitation. Chromatographic techniques separate the constituents into temporally separated peaks in a single stream either continuously passing detection means or fractionally collecting for later quantitation. Practical electrophoretic separation methods involve separation in a porous solid medium followed by staining or enzyme reaction of the separated molecules at rest. Densitometry of the colored portions is then used for quantitation. These methods are labor intensive, awkward and imprecise. They require skills not available at all hours. Because some of these analyses are required for emergency diagnosis such as heart attacks. A fast, accurate automatic system available at all hours would be a new and useful contribution.

SUMMARY OF THE PRESENT INVENTION

One object of the present invention is to provide an apparatus and method for automatic isoenzyme analysis that is simple to operate, relatively foolproof, reliable, consistent, direct reading, fast action, conservative of expensive reagents, available at all hours, fast easy changeover from one enzyme to another so that on a single sample it becomes practical to perform CPK and then LDH instead of batching multiple samples and running CPK on all of them and then changing to LDH. It is a further object of the invention that new enzyme assays are easily added to the repertory. It is a further object that automatic means be provided for removing interfering materials from the sample to improve enzyme analysis. It is a further object that means be provided for separating the isoenzymes into separate moving streams. It is a further object that means be provided for admixing reagents with said streams of separated enzymes. It is a further object that means be provided to control temperature of said mixtures. It is a further object that means be provided to measure changes in optical properties of said mixtures. It is a further object that data processing means be provided to convert optical measurements into useful data readout. It is a further object of the invention that it provide a wide range of sensitivities so that very low values can be measured and very high values can also be measured before reagent is exhausted and require dilution and repeat analysis.

Amphoterism is a property of amino acids, polypeptides, proteins (of which enzymes are a class), and many other clinically important constituents of body fluids. Ampholytes (amphoteric electrolytes) dissociate both as acids and as bases depending upon the pH of the solution. If an ampholyte in solution is placed in an electric field, the molecules will migrate to one electrode or the other in accordance with the pH of the solution. At a given pH, the molecule behaves neither as an acid nor as a base and does not migrate to anode or cathode. This is called the isoelectric point. It is usually expressed in terms of the pH of the solution at which this occurs. In the isoelectric state the ampholyte is though to be dissociated both as an acid and as a base and fails to appear electrically charged because its positive and negative charges are equal i.e. net charge is zero. When acid is added the ampholyte behaves as a base with a net positive charge; when alkali is added, it behaves as an acid with a net negative charge.

It is an object of the present invention to control and select the migration and separation of different molecules by adjustment of the pH of the streams moving through the electroseparation means of copending application Ser. No. 972,670. It is a further object of the present invention that means be provided to analyze a plurality of different molecules simultaneously using a plurality of said electroseparation means and serial adjustment of pH of the moving streams.

It is an object of the invention that simple detection means be provided for the quantitation of concentration of certain molecules in the separated streams. It is an object of the invention to provide the integrated optical cell of copending application Ser. No. 968,907, as a measuring means. Novel dispensing means conserves reagent and sample, provides automatic wash and prevents errors in selecting reagents.

The foregoing and other objects and advantages of the invention will be described more fully in the following detailed description of the invention.

BRIEF DESCRIPTION OF THE DRAWINGS

FIG. 1 is a schematic drawing of apparatus of the type to which the invention relates showing sample, buffer and reagent being aspirated into an automatic isoenzyme analyzer with direct result readout.

FIG. 2 is a cross section through an electrical separation module.

FIGS. 3 A,B,C,D show details of an integrated optical measuring means.

FIGS. 4 A,B,C show sample and reagent dispensing and storing means.

DESCRIPTION OF THE PREFERRED EMBODIMENTS

In FIG. 1, peristaltic pump 1 pulls fluid at precise rates through flexible tubing lines 2, thereby metering these fluids. Four of these lines originate in sample pipet 3, first buffer pipet 4, second buffer pipet 5 and reagent pipet 6, shown immersed in their respective liquids in individual containers. Reagent 9 and buffers 10 and 11 are held at reduced temperature by temperature means 12. Analysis is begun by addition of buffer 10 to sample 13 and mixing in mixing coil 14. This adjusts sample pH to a point intermediate the isoelectric point of CPK (creatine phosphokinase) MM and CPK MB. At this pH, the MM fraction will have a net positive charge and migrate to the cathode in an electric field and CPK MB and CPKBB will be negatively charge and migrate anodically. The pH adjusted mixture passes into central channel 15 of a first electroseparation stage 16 of the type described in copending application Ser. No.

972,670. Membranes 17 are of a pore size large enough to permit passage of enzymes, and membranes 19 are of a size small enough to prevent passage of enzymes. Cathode 20 is immersed in cathode fluid stream 21, and anode 22 is immersed in anode fluid stream 23. The positively charged CPK MM fraction will migrate cathodically from central channel 15 across membrane 17 to recipient channel 25.

It will be prevented from migrating all the way to the cathode by pore size limitation of membrane 19. The negatively charged CPKMB and CPKBB fractions will migrate anodically to recipient channel 24. Second buffer 11 is mixed with the CPKMB and CPKBB stream in mixing coil 14 to adjust the mixture to a pH intermediate the isoelectric points of CPKMB and CPKBB. The mixture passes into central channel 26 of second electroseparation module 27. The now positively charged CPKMB fraction will migrate cathodically into recipient channel 25 while the still negatively charged CPKBB fraction migrates anodically into recipient channel 24. The use of extra electrode channels separated from recipient channels by small pore membranes preventing migration of the analyte is a means of preventing electrode effects from adversely affecting analyte. Color forming enzyme substrate reagent 9 is pumped and mixed with each of the three separated streams in mixing coils 14 maintained at low temperature to reduce substrate depletion prior to measurement. The three cooled and mixed streams of enzyme and substrate next enter temperature controlled (37° C.) three channel optical detector wherein optical properties and their change with time are detected by light sources 29 and light sensors 30. These view the stream contents at progressively increasing time intervals. Signals from the sensors are connected by wires not shown to data processor 31 wherein enzyme levels of each fraction are computed and displayed on display 32. Progressively increasing time intervals of measurement provide the short intervals needed for high enzyme concentration before substrate is exhausted and the long intervals required for low enzyme concentration.

In other embodiments of the invention a preliminary electroseparation step may be incorporated to remove interfering materials. When conditions permit, a mixture may be separated into three streams in a single electroseparation process by adjusting the pH to the isoelectric point of an intermediate component which will tend to remain in the central channel while positively and negatively charged components will move into cathode and anode recipient channels respectively.

FIG. 2 is a sectional view of electric separation module. Rigid and thick upper member 34 and lower member 35 and thin members 36, 33 and 39 are bolted together with bolts sandwiching in thin membranes 40, 41, 42 and 43. Top member 34 has groove 44 on its underside terminating at tubes 45 and 46. Bottom member 35 has groove 47 on its upper surface terminating in tubes 45 and 46. Center member 36 has slot which connects with tubes 49 and 50 in top member via 2 holes in membranes. When membranes are tightly compressed by bolts, the grooves and slots are sealed so that five parallel channels are formed through which fluid may be passed. The central channel 51 terminates at reagent mixture inlet 49 and outlet 50. Membrane 40 forms a common wall that channel 51 shares with upper recipient channel 52, and membrane 41 forms a common wall that channel 51 shares with lower recipient channel 53. Upper recipient channel 52 terminates in recipient inlet 54 and outlet 55. Lower recipient channel 53 terminates in recipient inlet 56 and outlet 57. Electrode 59 in upper electrode channel 60 and electrode 61 in lower electrode channel 60 are connected to negative and positive voltage respectively. In the assembly of the separator, sharp locator pins 62, fastened to lower member 35 transfix the membranes and pass through holes in members to facilitate alignment during assembly. Holes are punched in members and membranes as indicated to permit fluid flow.

FIG. 3 shows structural details of an optical detector for measuring four temperature controlled flowing fluid streams at six serial time intervals after mixing and temperature adjustment. FIG. 3D is a diagrammatic side view of the assembled components. For clarity, the components are not drawn tightly together so as to be leak proof as they would be in normal operation by bolts through locator holes 78. Uniform light source 79 illuminates filter 80 to select particular wavelength of light to pass through rotating occulter 81, which is an opaque disc driven by stepping motor 82 with at least one small opening 125 for light to pass through a hole 83 in opaque clamp mask 84. Light then travels through flat transparent plate 85 of an inert material such as quartz. It then passes through hole 86 which is actually part of a slot 87 in flat plate 88. It then passes through hole 89 in metal plate 90. It next passes through hole 91 which is actually part of slot 92 in flat plate 93. Light then passes through flat transparent plate 94. It then passes through a hole in opaque clamp mask 95, whereupon it impinges upon light sensing means 96, either directly or through directing means such as lenses or mirrors. In the event fluorescense is being measured, a second filter is interposed between fluid cell and sensing means. The foregoing description followed the light path through a single hole. For clarity only this single optical cell out of the twenty four is shown in FIG. 3D. Multiple light paths are provided to sequentially view and measure the contents of the four moving fluid streams at successive time intervals after mixing and temperature adjustment. The stepping motor 82 positions the occulter 81 so that only a single light path is illuminated at any one time. As motor steps, each light path is viewed in turn. A single light source and sensing means thereby serves multiple light paths and multiple fluid streams by a time sharing approach. A computer clock pulse can trigger the stepping motor and also sample and hold and analog to digital converter means at the signal output of light sensor means, thereby allowing a single signal path to serve all the elements for additional economy. A single switch means on the occulter provides light path location information to the computer once each revolution so that signals will be correctly synchronized. FIG. 3C is a plan view of flat metal plate 90 which is of a thermally conductive metal such as copper. It has the two locating holes 78 in common with other detector components to aid in alignment and assembly. The circular row of holes 89 form the cylindrical bodies of the optical flow cells. Inlet holes 97 and outlet holes 98 have metal tubes 99 projecting from their tops, better seen in side view of FIG. 3D. These tubes may have their inside bores rifled to create a swirling motion in fluid moving therein to promote heat transfer and mixing. An accessory heating means, not shown, may be connected to inlet tubes at a higher temperature to promote more rapid thermal equilibrium of the incoming fluid. The above holes all pass through from top to bottom of the plate and may be coated inside with a non reactive material such as gold plating. Heating elements 100 and temperature sensor 101 are connected to control means not shown to maintain plate 90 at the desired reaction temperature. FIG. 3B is a plan view of upper flat plate 88, and FIG. 3A is a plan view of lower flat plate 93. These are made of thin, hard inert material such as Corning Fotoform or Fotoceram. The various shaped slots go through from top to bottom faces of the thin plates. They form the side walls of fluid channels connecting the various holes in metal plate 90. The top and bottom walls of the channels are formed by one of the transparent plates 85 or 94 and either the top or bottom face of metal plate 90. Only the metal plate is thermally conductive, the other walls are insulating, therefor heat transfer is with the metal plate. First slot 102 in plate 93 is convoluted to provide improved mixing and heat transfer to incoming fluid. It connects inlet tube 99 to first optical cell hole 89, and incoming fluid must be thermally equilibrated promptly. Fluid proceeds up hole 89 in metal plate 90 to slot 86 in plate 88. This carries it to second hole 103 in metal plate. It goes down this hole to slot 92 in bottom plate 93, which carries it to third hole 104 in metal plate. It goes up the hole to slot 108 in plate 88 which carries it to fourth hole 105 in metal plate. It goes down this hole to slot 110 in plate 93, which carries it to fifth hole 106 in metal plate. It goes up this hole to slot 109 in plate 88, which carries it to sixth hole 107 in metal plate. It goes down this hole to slot 111 in plate 93 which carries it to outlet tube 99 in the metal plate. As the fluid proceeds from the first to the sixth hole it will be noted that the connecting channels formed by the slots in plates 88 and 93 become longer and longer. This provides progressively longer time intervals between optical readings. This non linear sampling method allows a wide range of sensitivity and multiple samplings for reading the proper part of the dynamic enzyme curve while the actual light readings are made at uniform time intervals.

FIG. 4A shows a side view of a sample and reagent dispensing means for providing input fluids into the analyzer. Tubing lines from peristaltic pump terminate at aspiration pipets for sample 63, buffer 64, and reagent 65. Additional buffers or other reagents would be provided for in similar fashion. These project below support plate 66 which also supports pulleys 67. Support plate 66 is suspended above base plate 69 by two vertical guide rods 70 and two sloping guide rods 71. Container carrier 72 is slideably connected to vertical guide rods 70 which pass through holes 73 in carrier. FIG. 4B is a plan view of said carrier. Turntable 74 rotates about bearing 75 mounted in carrier 72. Said turntable is hand rotatable to one of four positions fixed by detent 76 and notches 77. Sample container is held by spring fingers in center hole 111 designed to accomodate a wide variety of containers. Sample container remains unchanged by any rotation of the turntable. When carrier 72 is raised to the support plate, sample pipet 63 will enter said sample container, because guide rods restrict movement of carrier to the vertical. In each of the four rotational positions of said turntable, a different set of one buffer container 112 and one reagent container 113 are positioned under their respective pipets. When the carrier 72 is raised to the upper position, these pipets 64 and 65 will enter their containers and aspirate their contents. Each of the four rotational positions of said turntable and each set of containers is used for a different enzyme analysis. One position and container set may be used for CPK analysis and another for LDH. A third may be used for phosphatase analysis. A window 114 in the side of carrier 72 displays the selected analysis to the operator. In addition a row of four analysis selecting switches 115, one for each selected analysis is mounted beneath support plate 66. This is shown in underside detail of plate 66 in FIG. 4C. Each one of said switches represents a different analysis. When actuated, the switch communicates to the computer which of the four sets of containers is being aspirated so that the computer can select the appropriate operating program. It may also begin an aspiration timer to signal when it has had enough fluid for an adequate sample. On the periphery of said turntable are mounted four position indicating fingers 116. They are so located that one of them will actuate the appropriate one of the four analysis selecting switches when carrier is in aspirate position. This eliminates operator effort and error. To further reduce operator error, each container hole 117 in said turntable is of a different shape. The outside of each container is shape coded so that it can fit into only the correct hole. The sensitive reagents employed in these analyses often deteriorate rapidly at room temperature. In order to maintain an instrument ready at all times, and reduce operator labor, this invention provides reagent cold storage means for reagents in operating position. This also provides means for mixing reagents with enzymes at reduced temperature to avoid substrate depletion before measurement. Refrigeration means 119 cools metal plate 120 in base plate. Base of turntable is a thermally conductive block 121 which rests upon cold plate 120 cooling containers which rest in holes in said block 121. For ease of fabrication the holes may be round and a thin plate with special shape coded holes cut therein fastened to the top. The carrier may be insulated. To reduce the carryover from one sample to the next, a washing and air segmentation step is provided by wash carrier 122 which slides up and down sloping guide rods 71 fitting in holes 73 in said carrier. In the uppermost position against support plate 66, all aspirating pipets are immersed in wash liquid and wash liquid is pumped through all lines, purging them of preceeding sample. In this position, said carrier actuates wash timer switch 123. When washing is complete, the operator is signalled. A cable 124 runs from reagent carrier 72, around the two pulleys 67 to wash carrier 122. It is of such a length that when one carrier is in aspirating position, the other rests on the base plate. Reagent carrier 72, being heavier, will rest on baseplate when the instrument is unattended, leaving it in wash mode while operator inserts another sample, selects analysis or performs unrelated duties. When reagent carrier is lifted by hand to aspirate position, wash carrier falls to base plate. Operator must hold the carrier in this position until signalled cycle is complete, whereupon operator lowers it. This method consumes valuable reagent only as needed. Every time a carrier is lowered, a bubble of air is aspirated. This air segmentation contributes to wash process. When a large number of samples are to be analyzed at one time, any of the automatic sample devices in common use or the one described in the copending parent application #898,998 may be employed.

By changing electroseparator voltage, reversing it or applying diverse voltage waveforms, changes in the properties of the analyzer may be accomplished by a simple computer instruction.

While I have shown and described the preferred embodiments of my invention, it will be understood that the invention may be embodied otherwise than as herein specifically illustrated or described, and that certain changes in the form and arrangement of parts and in the specific manner of practicing the invention may be made without departing from the underlying ideas or principles of this invention within the scope of the appended claims.

What is claimed is:

1. Apparatus for analysis of molecules in a sample fluid mixture in a flowing stream comprising: means for moving said sample fluid mixture in a flowing stream; separation means for separating certain molecules in said mixture into separate flowing streams on the basis of differential movement of said molecules by electrical force across membrane means, wherein said separate flowing streams are separated from one another by permeable or semi permeable membrane means; and measuring means disposed at at least one of said separate streams to measure concentration of particular molecules in fluid in said separate stream.

2. Apparatus of claim 1, wherein a first reagent means is provided to render said molecules more separable.

3. Apparatus of claim 1, wherein reagent means is provided to bring certain molecules to or near their isoelectric point to facilitate separation.

4. Apparatus of claim 1, further comprising at least one additional of said separation means serially connected to at least one said separated stream.

5. Apparatus of claim 4, wherein reagent means is provided to change the pH of said separated stream prior to passage into a serially connected separation means to facilitate separation.

6. Apparatus of claim 1, including means for dispensing sample liquid; means for dispensing at least one reagent; and means for mixing said liquids in a flowing stream.

7. Apparatus of claim 1, including reagent means to provide reagent to at least one of said separated streams to facilitate measurement.

8. Apparatus of claim 1, including a plurality of measuring means disposed along the length of at least one of said separated streams for measuring change in stream composition with time as fluid flows successively past said measuring means.

9. Apparatus of claim 8, including a first temperature control means to reduce measuring reaction prior to said stream passing said measuring means.

10. Apparatus of claim 1, including a second temperature control means to control temperature of said stream while passing said measuring means.

11. The invention of claim 1, wherein said separation means comprises: a central channel means through which flows a fluid mixture to be separated for analysis; at least one additional parallel recipient flow channel means adjacent said central channel and separated therefrom along its length by membrane means, said membrane means being sufficiently permeable to allow passage of at least one of the types of molecules to be separated; electrode means in at least two of said channels; electrical means for applying a difference of electrical potential across said electrode means, said potential applying a driving force to move certain molecules, having a net electrical charge, across said membrane means, thereby moving certain molecules from the fluid moving in one channel into the fluid moving in another channel.

12. The invention of claim 1, wherein measuring means comprises: upper and lower window means; a center plate means having multiple holes therethrough; outer plate means on either side of said center plate means having shaped slots, said slots connecting said holes in said center plate means to provide fluid flow channel means, said channel means having multiple optical cells formed by said holes, said slots and said window means.

13. The invention of claim 6 wherein dispensing means comprises: temperature controlled reagent holding means; sample holding means connected to said reagent holding means to supply sample and reagent simultaneously for dispensing; wash liquid means connected to said reagent holder means by alternating presenting means, said presenting means providing aspiration of reagent and sample in a first mode and providing aspiration of wash liquid in an alternating second mode.

14. Invention of claim 13, including means for automatic change to wash liquid when said dispensing means is released by the operator.

15. Invention of claim 13 wherein reagent holding means includes: shape coded apertures in said holding means; shape coded containers fitting said apertures to assure correct positioning of reagents; means for moving said holding means to position particular reagent containers for aspiration; and position indicating means connected to said reagent holding means to signal to associated apparatus the particular reagent containers in position for aspiration.

* * * * *